(12) United States Patent
Wong et al.

(10) Patent No.: US 7,745,196 B1
(45) Date of Patent: Jun. 29, 2010

(54) METHODS AND COMPOSITIONS FOR IDENTIFYING PEPTIDE MODULATORS OF CELL SURFACE RECEPTORS

(75) Inventors: Brian Wong, Los Altos, CA (US); Donald G. Payan, Hillsborough, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 1017 days.

(21) Appl. No.: 11/067,065

(22) Filed: Feb. 25, 2005

Related U.S. Application Data

(60) Provisional application No. 60/556,531, filed on Mar. 25, 2004.

(51) Int. Cl.
*C12N 1/00* (2006.01)
*G01N 33/53* (2006.01)

(52) U.S. Cl. .................................. 435/243; 435/7.1

(58) Field of Classification Search ............... None
See application file for complete search history.

(56) References Cited

U.S. PATENT DOCUMENTS

| | | | |
|---|---|---|---|
| 6,455,247 | B1 | 9/2002 | Nolan |
| 6,562,617 | B1 | 5/2003 | Anderson |
| 2002/0150912 | A1 | 10/2002 | Owman |
| 2004/0014100 | A1 | 1/2004 | Lorenz |

FOREIGN PATENT DOCUMENTS

WO    WO02/090535 A1  *  11/2002

OTHER PUBLICATIONS

Harley et al. (Journal of Biological Chemistry. Oct. 4, 1996; 271(4): 24625-24633).*
Angeloni et al., The Soluble SEMA Domain of the RON Receptor Inhibits Macrophage-Stimulating Protein-Induced Receptor Activation, J. Biol. Chem., 2004, 279:3726-32.
Chang et al., A General Method for Facilitating Heterodimeric Pairing Between Two Proteins: Application OT Expression of α and β T-Cell Receptor Extracellular Segments, Proc. Natl. Acad. Sci., 1994, 91:11408-12.
Deller et al., Cell Surface Receptors, Curr. Opin. Struct. Biol., 2000, 10:213-9.
Gray et al., Cloning of Human Tumor Necrosis Factor (TNF) Receptor CDNA and Expression of Recombinant Soluble TNF-Binding Protein, Proc. Natl. Acad. Sci. 1990, 87:7380-7384.
Gregoire et al., Engineered Secreted T-Cell Receptor αβ Heterodimers, Proc. Natl. Acad. Sci., 1991, 88:8077-81.
Ishii et al., Preparation of Soluble Recombinant T Cell Receptor α Chain by Using a Calmodulin Fusion Expression System, J. Immunol. Methods, 1995, 186:27-36.
Kinsella et al., Retrovirally Delivered Random Cyclic Peptide Libraries Yield Inhibitors Fo Interleukin-4 Signaling in Human B Cells, J. Biol. Chem., 2002, 277:37512-8.
Minor et al., Assays to Measure the Activation of Membrane Tyrosine Kinase Receptors: Focus on Cellular Methods, Curr. Opin., Drug. Discov. Devel., 2003, 6:760-5.
Parks et al., Topology of Eukaryotic Type II Membrane Proteins: Importance of N-Terminal Positively Charged Residues Flanking the Hydrophobic Domain, Cell, 1991, 64:777-87.
Parks et al., Role of $NH_2$-Terminal Positively Charged Residues in Establishing Membrane Protein Topology, J. Biol. Chem., 1993, 268(25):19101-19109.
Schodin et al., Binding Properties and Solubility of Single-Chain T Cell Receptors Expressed in *E. Coli*, Mol. Immunol., 1996, 33:819-29.
Tsimberidou et al., Pilot Study of Recombinant Human Soluble Tumor Necrosis Factor (TNF) Receptor (P75) Fusion Protein (TNFR:FC; ENBREL) in Patients With Refractory Multiple Myeloma: Increase in Plasma TNFα Levels During Treatment, Leuk. Res., 2003, 27:375-80.

* cited by examiner

*Primary Examiner*—Scott Long
(74) *Attorney, Agent, or Firm*—James S. Keddie; Carol L. Francis; Travis Young

(57) ABSTRACT

The invention provides methods and compositions for identifying modulators, particularly peptide modulators, of cell surface receptor activity. Specifically, the invention provides a cell containing a recombinant nucleic acid encoding a polypeptide modified for intracellular presentation, which cell may further comprise one or both of a recombinant nucleic acid encoding a binding partner for that polypeptide and recombinant nucleic acid encoding a test polypeptide. The subject cell may be a member of a library of cells, and the library may be used in screening methods for identifying test polypeptides (e.g., conformationally restrained polypeptides) having cell surface receptor modulatory activity. The invention finds use in a variety of drug-discovery applications.

35 Claims, No Drawings

METHODS AND COMPOSITIONS FOR IDENTIFYING PEPTIDE MODULATORS OF CELL SURFACE RECEPTORS

FIELD OF THE INVENTION

The present invention generally relates to methods and compositions for use in identifying agents that modulate cell surface receptor activity. Specifically, the invention relates to compositions and screening methods for identifying peptide modulators of cell surface receptor activity.

BACKGROUND OF THE INVENTION

Extracellular signaling molecules are typically hydrophilic and do not generally cross the hydrophobic plasma membrane of a cell by simple diffusion. Accordingly, extracellular signaling molecules are usually specifically bound by receptors that are situated on the surface of a target cell (i.e., "cell surface receptors"), and binding of a signaling molecule to a cell surface receptor modulates activity of the receptor to initiate a signal in the target cell.

Cell surface receptors play a pivotal role in almost every aspect of cell biology. Because of this role, as well as their accessibility to hydrophilic molecules, cell surface receptors have become an attractive target for drug discovery. Because peptides are relatively small, hydrophilic (making them easily formulated for administration), and can be made in large quantities either synthetically or recombinantly, peptide modulators are in particularly great demand.

Non-naturally occurring modulators of a particular cell surface receptor are typically identified from a large library of candidate agents (a library having, e.g., $10^6$-$10^9$ different compounds). Each member of such a library is typically assayed for receptor modulatory activity, and receptor modulators are identified using the assay. Assuming the sensitivity of the assay is not limiting, the success of such screening assays primarily depends on the size of the library of candidate agents screened: the larger the library used, the more modulatory agents will be identified. Accordingly, in view of the great demand for peptide modulators of cell surface receptor activity, there is a also great demand for methods of screening large peptide libraries to identify those peptides.

However, libraries containing large numbers (e.g., $10^7$-$10^{12}$) of candidate peptides are generally prohibitively expensive to make, and, as such, are generally not available. For example, assuming that a single peptide can be synthesized in an amount suitable for assaying for the cost of $10, a library of $10^7$ peptides would cost $100M. As such, while there is a great need for methods of identifying peptide modulators of cell surface receptor activity, this need is generally unmet because large libraries of candidate peptides are not generally available.

Accordingly, a great need still exist for methods of identifying peptide modulators of cell surface receptor activity. The invention described herein meets this need, and others.

LITERATURE

Literature of interest includes: Minor (Curr. Opin. Drug. Discov. Devel., 2003, 6:760-5), Deller et al. (Curr. Opin. Struct. Biol., 2000, 10:213-9); Gray et al. (Proc. Natl. Acad. Sci. 1990 87:7380-7384), Tsimberidou et al. (Leuk. Res. 2003 27:375-80), Ishii et al. (J. Immunol. Methods 1995 186:27-36), Chang et al. (Proc. Natl. Acad. Sci. 1994 91:11408-12), Gregoire et al., (Proc. Natl. Acad. Sci. 1991 88:8077-81), Schodin et al. (Mol. Immunol. 1996 33:819-29), Angeloni et al. (J. Biol. Chem. 2004 279:3726-32), Parks and Lamb (J. Biol. Chem. 1993 268:19101-19109), Parks (Cell 1991 64:777-87), Harley and Tipper (J. Biol. Chem. 271:24625 and 24633) Kinsella et al. (J. Biol. Chem. 2002 277:37512-8); Published U.S. Patent Applications 20040014100 and 20020150912; and U.S. Pat. Nos. 6,562, 617 and 6,455,247.

SUMMARY OF THE INVENTION

The invention provides methods and compositions for identifying modulators of cell surface receptor activity. Specifically, the invention provides a cell containing a recombinant nucleic acid encoding a polypeptide modified for intracellular presentation and a recombinant nucleic acid encoding a binding partner for that polypeptide. The cell may also contain a recombinant nucleic acid encoding a candidate agent, such as a conformationally restrained test polypeptide. The subject cell may be a member of a library of cells, and the library may be used in screening methods for identifying, for example, conformationally restrained polypeptides having cell surface receptor modulatory activity. The invention finds use in a variety of drug-discovery applications.

Also provided is a method for identifying a cell producing a biologically active conformationally restrained polypeptide. In general, this method involves: a) assaying a plurality of pools of different cells, the cells of each pool producing a plurality of different conformationally restrained test polypeptides, b) identifying a pool of cells producing a biologically active conformationally restrained test polypeptide, c) separating the cells in the identified pool, and d) assaying the isolated cells to identify a single cell producing a biologically active conformationally restrained test polypeptide. In many embodiments, the method involves lysing samples of cells from the pools of cells to make cell lysates, and assaying the lysates for biological activity. The invention finds use in a variety of drug-discovery applications.

DEFINITIONS

Before the present invention is further described, it is to be understood that this invention is not limited to particular embodiments described, as such may of course vary. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this invention belongs.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Throughout this application, various publications, patents and published patent applications are cited. The disclosures of these publications, patents and published patent applications referenced in this application are hereby incorporated by reference in their entirety into the present disclosure. Citation herein by Applicant of a publication, patent, or published patent application is not an admission by Applicant of said publication, patent, or published patent application as prior art.

It must be noted that as used herein and in the appended claims, the singular forms "a", "and", and "the" include plural referents unless the context clearly dictates otherwise. Thus, for example, reference to "a polypeptide" includes a plurality of such polypeptides, and reference to "the cell surface receptor" includes reference to one or more cell surface receptors and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

A "biopolymer" is a polymer of one or more types of repeating units, regardless of the source. Biopolymers may be found in biological systems and particularly include polypeptides and polynucleotides, as well as compounds containing amino acids, nucleotides, or analogs thereof.

The terms "polypeptide" and "protein" are used interchangeably throughout the application and mean at least two covalently attached amino acids, which includes proteins, polypeptides, oligopeptides and peptides. A polypeptide may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. Normally, the amino acids are in the (S) or L-configuration. If non-naturally occurring side chains are used, non-amino acid substituents may be used, for example to prevent or retard in vivo degradation. Naturally occurring amino acids are normally used and the protein is a cellular protein that is either endogenous or expressed recombinantly. Conformationally restrained polypeptides are encompassed by the term "polypeptide".

In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 10, 20, 30, 40 or 50 amino acids. In certain embodiments, peptides are between 5 and 30 amino acids in length.

The term "fusion protein" or grammatical equivalents thereof is meant a protein composed of a plurality of polypeptide components, that while typically unjoined in their native state, typically are joined by their respective amino and carboxyl termini through a peptide linkage to form a single continuous polypeptide. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunologically tag, a detectable fusion partner, such as a fluorescent protein, P-galactosidase, luciferase, etc., and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular and may contain modifications in the backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick").

By the term "recombinant nucleic acid" herein is meant nucleic acid not normally found in nature. In general, a "recombinant nucleic acid" is originally constructed in vitro, e.g., by the manipulation of nucleic acid by endonucleases. Thus an isolated nucleic acid in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations. However, such nucleic acids, once produced recombinantly, although subsequently replicated non-recombinantly, are still considered recombinant for the purposes of the invention.

The term "endogenous", when used in reference to a biopolymer, means that which is naturally produced (e.g., by an unmodified mammalian or human cell). As used herein, the terms "endogenous" and "native" are interchangeably.

A "deletion" is defined as a change in the sequence of a biopolymer in which one or more residues are absent as compared to a sequence of a parental biopolymer. A deletion can remove about 2, about 5, about 10, up to about 20, up to about 30 or up to about 50 or more amino acids. A biopolymer may contain more than one deletion.

An "insertion" or "addition" is a change in a sequence of a biopolymer that results in the addition of one or more residues, as compared to a sequence of a parental biopolymer. "Insertion" generally refers to addition to one or more residues within a biopolymer, while "addition" can be an insertion or refer to amino acid residues added at an end, or both termini, of a biopolymer. An insertion or addition is usually of about 1, about 3, about 5, about 10, up to about 20, up to about 30 or up to about 50 or more amino acids. A biopolymer may contain more than one insertion or addition.

A "substitution" results from the replacement of one or more residues of a biopolymer by different residues, as compared to a sequence of a parental biopolymer. It is understood that a polypeptide may have conservative amino acid substitutions which have substantially no effect on activity of the polypeptide. By conservative substitutions is intended combinations such as gly, ala; val, ile, leu; asp, glu; asn, gln; ser, thr; lys, arg; and phe, tyr.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

The term "isolated" also means that the recited material is usually unaccompanied by at least some of the material with which it is normally associated in its natural state, preferably constituting at least about 0.5%, more preferably at least about 5% by weight of the total protein in a given sample. "Purified" means that the recited material comprises at least about 75% by weight of the total protein, with at least about 80% being preferred, and at least about 90% being particularly preferred.

As used herein, the term "substantially pure" refers to a compound that is removed from its natural environment and is at least 60% free, preferably 75% free, and most preferably 90% free from other components with which it is naturally associated.

A "coding sequence" or a sequence that "encodes" a selected polypeptide, is a nucleic acid molecule which can be transcribed (in the case of DNA) and translated (in the case of mRNA) into a polypeptide, for example, in a host cell when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or prokaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Operably linked" refers to an arrangement of elements wherein the components so described are configured so as to perform their usual function. In the case of a promoter, a promoter that is operably linked to a coding sequence will effect the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring nucleic acids into to a host cell. Typically, "vector construct," "expression vector," and "gene transfer vector," mean any nucleic acid construct capable of directing the expression of a nucleic acid of interest and which can transfer nucleic acid sequences to host cells. This can be accomplished by genomic integration of all or a portion of the vector, or transient or inheritable maintenance of the vector as an extrachromosomal element. Thus, the term includes cloning, and expression vehicles, as well as integrating vectors.

An "expression cassette" encompasses any nucleic acid for directing expression of a coding sequence of interest. In most embodiments, express cassettes contain a coding sequence operably linked to an expression-regulatory sequence, e.g., a promoter. Such cassettes can be constructed in a vector in order to transfer the expression cassette into a host cell.

A polynucleotide is "derived from" a particular cell if the polynucleotide was obtained from the cell. A polynucleotide may also be "derived from" a particular cell if the polynucleotide was obtained from the progeny of the cell, as long as the polynucleotide was present in the original cell. As such, a single cell may be isolated and cultured, e.g., in vitro, to form a cell culture prior to isolating a nucleic acid from that cell.

The term "polypeptide modified for intracellular presentation", as will be explained in greater detail below, refers to a non-naturally occurring recombinant intracellular version of a naturally-occurring polypeptide that, in its naturally-occurring form, is usually present on the surface of a cell. Such a polypeptide, in its naturally-occurring form, is usually a cell surface-bound polypeptide that is anchored, typically via a transmembrane domain, to the plasma membrane of a mammalian cell. Polypeptides may be modified for intracellular presentation using a number of methods, as will be discussed in greater detail below. Cell surface receptors are a type of polypeptide that can be modified for intracellular presentation.

The term "cell surface receptor" refers to a class of receptors that is generally well known in the art (see review by Deller et al. Curr. Opin. Struct. Biol., 2000, 10:213-9). As will be explained in greater detail below, ion channel-linked receptors, G-protein-linked receptors, and enzyme linked receptors are types of cell surface receptors of interest described herein.

The terms "conformationally restrained polypeptide" and "conformationally restricted polypeptide" are used interchangeable herein to describe a polypeptide that contains covalent or non-covalent bonds between amino acids within the polypeptide (i.e., intramolecular bonds) and is restricted in its conformation. Amino acids within a conformationally restrained polypeptide are generable not able to freely rotate around their peptide bonds. Conformationally restrained polypeptides, and methods for making conformationally restrained polypeptides, are generally well known in the art (see, e.g., U.S. Pat. No. 6,596,485). A "cyclic peptide" is a type of conformationally restrained polypeptide that, as its name suggests, contains a cyclic polymer of amino acids. The term "cyclic peptide" encompasses peptides that are circularized via a peptide bond between the N and C terminal amino acids of a linear peptide (as described in U.S. published patent application 20040014100, for example), peptides that are circularized via an intramolecular disulfide bond, and other types of cyclic peptides. In certain embodiments, a cyclic peptide is circularized via a peptide bond, as discussed above. In other embodiments a cyclic peptide is circularized via a intramolecular disulphide bond. Peptides that are circularized via an intramolecular disulfide bond may be specifically excluded from the claims.

By "presentation structure" or grammatical equivalents thereof, is meant an amino acid sequence, which, when fused to test polypeptide, causes the test polypeptide to be conformationally restrained.

The term "test polypeptide" is a polypeptide to be tested for biological activity in an assay. At the time of testing, a test polypeptide may have known or unknown sequence.

The term "randomized amino acid sequence" refers to a polypeptide having an amino acid sequence that is at least partially randomized, including fully randomized. When made recombinantly, a library of polypeptides having randomized amino acid sequences usually contains polypeptides having any of the naturally occurring amino acids, or any subset thereof, present into at least one or all positions (e.g., at last 1, 2, 3, 4, 5, about 8, about 10, about 15, about 20, usually up to at least 100 or more positions) of the polypeptide. Polypeptide having a randomized amino acid sequence are usually produced using synthetic nucleic acids that contain any of the four nucleotides, or a subset thereof, at least one or all positions of the polynucleotide.

The term "specific binding" refers to the ability of a polypeptide to preferentially bind to a binding partner for that polypeptide that is present in a homogeneous mixture of different analytes. Typically, a specific binding interaction will discriminate between binding partners for a polypeptide and other analytes by more than about 10 to 100-fold or more (e.g., more than about 1000- or 10.000-fold). Typically, the affinity between a particular polypeptide and binding partner for the polypeptide when they are specifically bound in a polypeptide/binding partner complex is characterized by a $K_D$ (dissociation constant) of at least $10^{-6}$M, at least $10^{-7}$M, at least $10^{-8}$ M, at least $10^{-9}$ M, usually up to about $10^{-10}$ M.

The term "polypeptide/binding partner complex" is a complex that results from the specific binding of a polypeptide to a binding partner for the polypeptide, i.e., a "binding partner pair". A polypeptide and a binding partner for the polypeptide will typically specifically bind to each other under "conditions suitable for specific binding", where such conditions are those conditions (in terms of salt concentration, pH, detergent, protein concentration, temperature, etc.) which allow for binding to occur between the members of a binding partner pair in solution. Such conditions, particularly with respect to receptors and ligands, are well known in the art. Conditions suitable for specific binding typically permit specific binding of a polypeptide to a binding partner that have a dissociation constant ($K_D$) of less than about $10^{-6}$ M to each other, but not with other analytes.

A "library" of cells is a plurality of cells. Such a library may be a mixture of different cells, or may contain cells that are separated from each other (e.g., in the wells of a multi-well plate).

The terms "pool" or "mixture", as used herein, refers to a combination of elements, e.g., cells, that are interspersed and not in any particular order. A mixture is homogeneous and not spatially separable into its different constituents. Examples of mixtures of elements include a number of different cells that are present in the same aqueous solution. In other words, a mixture is not addressable. To be specific, an arrayed library of cells, as is commonly known in the art, is not a mixture of cells because the elements of the library are spatially distinct and the array is addressable.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms.

"Treatment" is also meant to encompass delivery of an agent in order to provide for a pharmacologic effect, even in the absence of a disease or condition. For example, "treatment" encompasses delivery of a receptor modulator that can provide for enhanced or desirable effects in the subject (e.g., reduction of pathogen load, beneficial increase in a physiological parameter of the subject, reduction of disease symptoms, etc.).

"Subject", "individual,", "host" and "patient" are used interchangeably herein, to refer to an animal, human or non-human, susceptible to or having a receptor-related disorder amenable to therapy according to the methods of the invention. Generally, the subject is a mammalian subject. Exemplary subjects include, but are not necessarily limited to, humans, non-human primates, mice, rats, cattle, sheep, goats, pigs, dogs, cats, and horses, with humans being of particular interest.

Other definitions of terms appear throughout the specification.

DETAILED DESCRIPTION OF THE INVENTION

The invention provides methods and compositions for identifying modulators, particularly peptide modulators, of cell surface receptor activity. Specifically, the invention provides a cell containing a recombinant nucleic acid encoding a polypeptide modified for intracellular presentation, which cell may further comprise one or both of a recombinant nucleic acid encoding a binding partner for that polypeptide and recombinant nucleic acid encoding a test polypeptide. The subject cell may be a member of a library of cells, and the library may be used in screening methods for identifying test polypeptides (e.g., conformationally restrained polypeptides) having cell surface receptor modulatory activity. The invention finds use in a variety of drug-discovery applications.

In one embodiment of particular interest, the subject screening methods involves assaying individual cells of a population of cells, where the individual cells contain: a) a recombinant nucleic acid encoding a first polypeptide modified for intracellular presentation, b) a recombinant nucleic acid encoding a binding partner for the polypeptide, and, c) a recombinant nucleic acid encoding a conformationally restrained test polypeptide. The assay is designed to identify a conformationally restrained polypeptide that modulates binding between the intracellular polypeptide and a binding partner for that polypeptide.

In further describing the invention in greater detail than provided in the Summary and as informed by the Background and Definitions provided above, the cellular compositions for use in the subject methods are described first, followed by a discussion of methods of screening using those compositions. This discussion is followed by a review of representative applications in which the subject methods find use.

Cellular Compositions

As mentioned briefly above, the subject invention provides a cell useful in screening assays for identifying biologically active polypeptides. In general, the subject cell contains recombinant nucleic acids encoding a polypeptide modified for intracellular presentation and one or both of a binding partner for that polypeptide, and a test polypeptide. In certain embodiments, the polypeptide modified for intracellular presentation and binding partner for that polypeptide form a detectable signal producing system that allows binding between the polypeptide and its binding partner to be monitored.

The cellular compositions of the invention are discussed in greater detail below.

Polypeptides of Interest

As mentioned briefly above, the subject cells contain a nucleic acid encoding a polypeptide modified for intracellular presentation. Polypeptides modified for intracellular presentation are non-naturally occurring intracellular versions of naturally-occurring cell-surface polypeptides, and, accordingly, may be described as "intracellularized" or "cytoplasmically presented" version of cell-surface polypeptides.

Cell surface polypeptides of interest are usually tethered to the surface of a cell by a membrane anchor, such as a hydrophobic transmembrane domain, that at least partially crosses the plasma membrane of a cell. Cell surface polypeptides of interest usually contain at least one domain ("an interaction domain") for interacting with an extracellular moiety, e.g., a signaling molecule that may be a polypeptide such as a peptide hormone, or any other type of moiety (e.g., a cell, a non-proteinaceous compound, etc.). Interaction domains are usually present on the outside of a cell and are accessible to moieties, particularly signaling moieties, that are also on the outside of the cell.

A cell surface polypeptide of interest may complex, e.g., dimerize, with another polypeptide to form a heterodimer, or may complex with itself to form a homodimer. Accordingly, in many embodiments of the invention, a cell surface polypeptide of interest typically has a binding partner to which it specifically binds. Depending on the polypeptide used in the subject methods, the binding partner also used in the subject methods may also be a polypeptide normally present extracellularly or on the outside of a cell (such as a ligand for the polypeptide), or another polypeptide present on the surface of the cell, e.g., a polypeptide that is similarly anchored to the cell surface or a subunit of a multi-subunit cell surface complex.

Cell surface receptors, i.e., cell surface polypeptides that are situated on the surface of a cell, bind extracellular signaling polypeptides, and transduce a signal to the interior of the cell are of particular interest. Cell surface receptors are generally well known in the art (and are reviewed by, e.g., Deller et al., (Curr. Opin. Struct. Biol., 2000, 10:213-9) and in Molecular Biology of the Cell (Alberts et al., 4$^{th}$ Edition, Garland Science, 2002 pages 871-892)), and need not be described exhaustively. Ligand-gated ion channels, G-protein coupled receptors and enzyme-linked cell-surface receptors are types of cell surface receptors of interest, and receptor tyrosine kinases, tyrosine-kinase-associated receptors, receptor-like tyrosine phosphatases, receptor serine/threonine kinases and receptor guanylyl cyclases are enzyme-linked cell-surface receptors of particular interest.

In particular, members of the TNF superfamily of tyrosine-kinase-associated receptors are of particular interest in the subject methods. Examples of TNF receptors that may be used in the subject methods include those that contain a death domain in their cytoplasmic tail (e.g., Fas, TNF-R1, DR3, TRAIL-R1, TRAIL-R2, and DR6), those that contain a TRAF-interacting motifs in their cytoplasmic tail (TNF-R2, CD40, CD30, CD27, LT-R, Ox40, 4-IBB, BAFF-R, BCMA, TACI, RANK, p75NGFR, HVEM, TNFRSF18, TROY, EDAR, XEDAR, RELT and Fn14), those that no contain any discernable intracellular signaling domain (e.g., TRAIL-R3, TRAIL-R4, decoy-R3 and osteoprotegerin), and others.

In particular embodiments, a single-subunit transmembrane receptor is employed in the subject methods. For example, a cytokine receptor (e.g., IL-4R, IL-2A, IL-15R, IL-13R and IL-17R, etc.), an antigen receptor (e.g., α/β T cell receptor, B cell receptor, γ/δ T cell receptor, etc.), a costimulatory receptor (e.g., CD28, B7.1, B7.2 or CTLA-4, etc.), a Toll-like receptor (e.g., TCR1, 2, 3, 4, 5, or 9) an integrin/adhesion molecule, or a receptor tyrosine kinase (e.g., EGFR, VEGFR, PDGFR, c-kit, etc.) may be employed in the subject methods.

As mentioned above, the invention features polypeptides modified for intracellular presentation, i.e., "intracellularized" versions of the above-referenced naturally occurring cell-surface polypeptides. Accordingly, in use, a naturally occurring cell surface polypeptide described above is typically modified to provide an intracellularized version of that polypeptide. Modification methods for use in intracellularizing a cell surface polypeptide according to the invention are generally well known in the art and include, for example, recombinantly producing a soluble form of an extracellular domain of the polypeptide within a cell. In these embodiments, the entire extracellular region of the polypeptide (usually a region that is between the transmembrane domain and the extracellular C- or N-terminus of the polypeptide) or a ligand-binding portion thereof, is produced within a cell. Any signal sequences that may be present in the native polypeptide may also be absent in the modified polypeptide. These methods have been generally used to produce soluble versions of cell surface polypeptides, particularly cell surface receptors, that maintain activity in that they are able to interact with a binding partner, e.g., a ligand. For example, Gray et al., (Proc. Natl. Acad. Sci. 1990 87:7380-7384), Tsimberidou et al., (Leuk. Res. 2003 27:375-80), Ishii et al., (J. Immunol. Methods 1995 186:27-36), Chang et al., (Proc. Natl. Acad. Sci. 1994 91:11408-12), Gregoire et al., (Proc. Natl. Acad. Sci. 1991 88:8077-81), Schodin et al., (Mol. Immunol. 1996 33:819-29) and Angeloni et al., (J. Biol. Chem. 2004 279: 3726-32) each report recombinant expression of soluble forms of ligand binding domains of various cell surface proteins, including the TNF receptor, and other cell surface receptors.

Cell surface polypeptides may be internalized by changing the orientation of the polypeptide in the plasma membrane. In other words, the extracellular domain of a cell surface polypeptide may be presented intracellularly by altering the direction that the polypeptide's transmembrane domain crosses the plasma membrane. In general, methods for so modifying a cell surface polypeptide involve identifying a transmembrane region of the polypeptide (which is also called the signal/anchor domain in many references) and altering the charge of the amino acids immediately proximal to the C- or N-terminus of the identified transmembrane domain. Typically, and as described in a number of publications (such as, e.g., Parks and Lamb, J. Biol. Chem. 1993 268:19101-19109; Parks, Cell 1991 64:777-87, Harley and Tipper, J. Biol. Chem. 271:24625 and 24633, and many others), the orientation of a transmembrane protein in a cell membrane is determined by the "charge difference rule" (Harley and Tipper, J. Biol. Chem. 271:24625-24633) in which the most positively charged end of a transmembrane region is usually present within the cell, and the most negatively charged end of the transmembrane region is usually translocated outside of the cell. Accordingly, any naturally-occurring transmembrane protein can be inverted with respect to the membrane by altering the charge of the domains immediately C- or N-terminal to a transmembrane region of the protein.

For example, for a transmembrane protein that has an N-terminal extracellular domain: a) substituting any negatively charged amino acids, e.g., Asp or Glu, with positively charged amino acids, e.g., Lys or Arg, in the 15 contiguous amino acids found immediately N-terminal to the N-terminus of the transmembrane domain of the protein, and/or b) substituting any positively charged amino acids, e.g., Lys or Arg, with negatively charged amino acids, e.g., Asp or Glu, in the 15 contiguous amino acids found immediately C-terminal to the C-terminus of the transmembrane domain of the protein, should result in a polypeptide modified for intracellular presentation. Likewise, for a transmembrane protein that has an C-terminal extracellular domain, a) substituting any negatively charged amino acids, e.g., Asp or Glu, with positively charged amino acids, e.g., Lys or Arg, in the 15 contiguous amino acids found immediately C-terminal to the C-terminus of the transmembrane domain of the protein, and/or b) substituting any positively charged amino acids, e.g., Lys or Arg, with negatively charged amino acids, e.g., Asp or Glu, in the 15 contiguous amino acids found immediately N-terminal to the N-terminus of the transmembrane domain of the protein, should result in a polypeptides modified for intracellular presentation. These methods are particularly applicable to Type I, Type II, Type III and Type IV transmembrane proteins. Signal sequences may or may not be present in the modified proteins.

In other embodiments, a subject polypeptide by transferring an isolated polypeptide into a cell. Methods for producing and isolating polypeptides are well known in the art (see, e.g., Sambrook, et al., Molecular Cloning: A Laboratory Manual, Third Edition, (2001) Cold Spring Harbor, N.Y.). Isolated peptides may be transferred into a cell by many known methods, e.g., by employing electroporation, microinjection and cationic lipids (e.g., liposomes). In certain embodiments, a subject polypeptide is mixed with the liposome reagent and is overlayed onto cultured cells. The liposome:protein complex fuses with the cell membrane or is internalized via an endosome. In certain other embodiments, a subject polypeptide may be internalized by fusing the polypeptide to an internalization domain. Such domains (or small protein transduction domains (PTDs) are well known in the art and are typically rich in basic amino acids (e.g., Lys and Arg-rich). Suitable include those of the HIV-1 TAT protein, the herpes simplex virus 1 (HSV-1) DNA-binding protein VP22, and the *Drosophila* Antennapedia (Antp) homeotic transcription factor.

In particular embodiments, a polypeptide modified for intracellular presentation may be fusion protein, and may contain, for example, a targeting sequence, affinity tag domain or a reporter domain that is a component of a signal-producing system.

Suitable affinity tags include any amino acid sequence that may be specifically bound to another moiety, usually another polypeptide, most usually an antibody. Suitable affinity tags include epitope tags, for example, the V5 tag, the FLAG tag, the HA tag (from hemagglutinin influenza virus), the myc tag, and the like, as is known in the art. Suitable affinity tags also include domains for which, binding substrates are known, e.g., HIS, GST and MBP tags, as is known in the art, and domains from other proteins for which specific binding partners, e.g., antibodies, particularly monoclonal antibodies, are available. Suitable affinity tags also include any protein-protein interaction domain, such as a IgG Fc region, which may be specifically bound and detected using a suitable binding partner, e.g. the IgG Fc receptor.

Suitable reporter domains include any domain that can report the presence of a polypeptide. While it is recognized that an affinity tag may be used to report the presence of a polypeptide using, e.g., a labeled antibody that specifically binds to the tag, light emitting reporter domains are more usually used. Suitable light emitting reporter domains include luciferase (from, e.g., firefly, *Vargula, Renilla reniformis* or *Renilla muelleri*), or light emitting variants thereof. Other suitable reporter domains include fluorescent proteins, (from e.g., jellyfish, corals and other coelenterates as such those from *Aequoria, Renilla, Ptilosarcus, Stylatula* species), or light emitting variants thereof. Light emitting variants of these reporter proteins are very well known in the art and may be brighter, dimmer, or have different excitation and/or emission spectra, as compared to a native reporter protein. For example, some variants are altered such that they no longer appear green, and may appear blue, cyan, yellow, enhanced yellow red (termed BFP, CFP, YFP eYFP and RFP, respectively) or have other emission spectra, as is known in the art. Other suitable reporter domains include domains that can report the presence of a polypeptide through a biochemical or color change, such as β-galactosidase, β-glucuronidase, chloramphenicol acetyl transferase, and secreted embryonic alkaline phosphatase. In some preferred embodiments, the reporter domain is *Renilla* luciferase (e.g., pRLCMV; Promega, catalog number E2661).

As will be described in greater detail below, such any reporter domain linked to a polypeptide modified for intracellular presentation may be a member of a signal producing system.

As mentioned above, the subject polypeptide may be fusion protein that contains a targeting sequence for localizing the polypeptide to a particular area of the cell. For example, targeting sequences for localizing a subject polypeptide to the nucleus, Golgi, endoplasmic reticulum, nucleus, nucleoli, nuclear membrane, mitochondria, chloroplast, secretory vesicles, lysosome and cellular membrane are well known in the art (see, e.g., U.S. Pat. No. 6,548,249 and many others) and need not be discussed here in any more detail.

The amino acid sequences of the subject polypeptides may contain further insertions, additions, deletions and substitutions, as desired. For example, in order to reduce undesirable disulfide bond formation, cysteine bonds in a polypeptide may be substituted for other amino acids. A linker, e.g., a flexible linker, may also be present in a subject polypeptide.

Binding Partners

As mentioned briefly above, the subject cells can contain a nucleic acid encoding a binding partner for the above-described polypeptide modified for intracellular presentation.

In general, once a cell surface polypeptide of interest has been identified, a binding partner for that polypeptide is typically also identified, usually by searching for the identity of the binding partner in public literature databases, several of which are dedicated protein-protein interaction databases (e.g., the NCBI/NLM PubMed database, UCLA's DIP database, the MINT datase (Zanzoni et al., FEBS Letters, 2002, 513; 135-140), or RIKEN's PPI database), or, alternatively, readily identified by one of many experimental tools (e.g., Fields et al., Nature (1989) 340:245-6; U.S. Pat. No. 5,667,973; Mendelsohn et al., Curr. Opin. Biotechnol. (1994) 5:482-6). Binding partners of interest include proteinaceous ligands and dimerization partners of cell surface polypeptides.

For example, in embodiments in which the subject intracellularized polypeptide is a modified cell surface receptor, the binding partner for that polypeptide may be a known peptide ligand for that receptor. Other binding partners include receptor subunits, and certain embodiments in which the binding partner of a subject intracellularized polypeptide is also a cell surface polypeptide, e.g., which forms a heterodimer with the receptor of interest. Such cell surface polypeptide-binding partners may also be modified for intracellular presentation as described above.

In general, a subject polypeptide modified for intracellular presentation, when produced within a cell, will specifically bind to a binding partner for that polypeptide when the binding partner is also produced within the same cell.

Like a subject internalized polypeptide, a binding partner of an internalized polypeptide may be a modified form of a native binding partner and may be a fusion protein, containing, for example, a targeting sequence, affinity tag domain, a reporter domain or any component of a signal-producing system, as discussed above and below. A linker, e.g., a flexible linker, may also be present in a subject binding partner.

Accordingly, an internalized polypeptide and binding partner for that polypeptide are usually modified versions of a naturally occurring cell surface polypeptide and naturally-occurring binding partner thereof. Typically, although not always, such a cell surface polypeptide and binding partner pair specifically bind to each other in non-recombinant cells.

Typically, the cell surface polypeptide and binding partner pair used in the subject methods are pre-determined, i.e., identified or chosen, prior to performing the subject methods. In other words, the identity of the cell surface polypeptide and binding partner used in the subject methods were known to specifically bind to each other before initiating the subject screening methods.

Signal Producing Systems

Although not necessary for practicing the invention because protein-protein interactions can be detected by a number of different methods (e.g., biochemical or physical means), the subject intracellularized polypeptide and the subject binding partner can form a detectable signal producing system for assaying their binding to each other in a cell. Accordingly, in many embodiments of the invention, the subject intracellularized polypeptide is a fusion protein containing a first component of a two component signal producing system, whereas the subject binding partner is a fusion protein containing the second component of that system. Signal producing systems of particular interest are those that produce a signal when the components of the system are in close proximity, e.g., bound in a complex such as the one formed between a subject polypeptide and a binding partner for that polypeptide.

In general, such a system may be a light emitting system (to provide an optically detectable signal), an enzymatic system, a cell survival system (e.g., a selectable or counterselectable marker system) or a transcription system, although several other types of system are well known and can be readily adapted to the subject methods.

Suitable light signal systems useful in the subject methods include Fluorescence Resonance Energy Transfer (FRET) and Bioluminescence Resonance Energy Transfer (BRET) systems. Fluorescent molecules having suitable emission and excitation spectra, when brought into close proximity with one another, can exhibit FRET. The fluorescent molecules are chosen such that the emission spectrum of one of the molecules (the donor molecule) overlaps with the excitation spectrum of the other molecule (the acceptor molecule). The donor molecule is excited by light of appropriate intensity within the donor's excitation spectrum. The donor then emits the absorbed energy as fluorescent light. The fluorescent energy it produces is quenched by the acceptor molecule. FRET can be manifested as a reduction in the intensity of the fluorescent signal from the donor, reduction in the lifetime of its excited state, and/or re-emission of fluorescent light at the longer wavelengths (lower energies) characteristic of the acceptor. When the fluorescent proteins physically separate, FRET effects are diminished or eliminated. (See, U.S. Pat. No. 5,981,200).

For example, a cyan fluorescent protein is excited by light at roughly 425-450 nm wavelength and emits light in the range of 450-500 nm. Yellow fluorescent protein is excited by light at roughly 500-525 nm and emits light at 525-500 nm. If these two proteins are placed in solution, the cyan and yellow fluorescence may be separately visualized. However, if these two proteins are in close proximity with each other, the fluorescent properties will be altered by FRET. The bluish light emitted by CFP will be absorbed by YFP and re-emitted as yellow light. This means that when the proteins are stimulated with light at wavelength 450 nm, the cyan emitted light is greatly reduced and the yellow light, which is not normally stimulated at this wavelength, is greatly increased.

FRET is typically monitored by measuring the spectrum of emitted light in response to stimulation with light in the excitation range of the donor and calculating a ratio between the donor-emitted light and the acceptor-emitted light. When the donor:acceptor emission ratio is high, FRET is not occurring and the two fluorescent proteins are not in close proximity. When the donor: acceptor emission ratio is low, FRET is occurring and the two fluorescent proteins are in close proximity. In this manner, the interaction between a first and second polypeptide fused to a first and second reactive module, wherein the first and second reactive modules are donor and acceptor fluorescent molecules, respectively, may be measured. As such, the two polypeptides of interest may contain a system that provides for FRET, e.g., one polypeptide contains GFP whereas the other contains YFP.

In another embodiment, the subject polypeptide and its binding partner provide a Bioluminescence Resonance Energy Transfer (BRET) system. In such a system, one polypeptide of interest produces (or destroys) a fluorescent product (or substrate) and the other polypeptide of interest is a fluorescent protein that undergoes resonant energy transfer with the fluorescent product (or substrate). In one embodiment, a BRET system comprises a luciferase from *Renilla* and a GFP. Exemplary BRET methodologies are described in Kroeger et al. (J. Biol. Chem. 2001 276:12736-43) and Xu et al. (Proc. Natl. Acad. Sci. 1999 96:151-6).

Suitable enzymatic systems include those that produce a color signal in the presence of a suitable substrate. Any suitable color producing system may be used, however, one suitable and widely used colorimetric assay suitable for use in the subject methods involves the alpha complementation system of LacZ. In general, these methods involve producing an inactive omega peptide of β-galactosidase, and complementing this peptide with an inactive alpha peptide of β-galactosidase, to form an active β-galactosidase enzyme. This system has been widely used to monitor a wide variety of protein-protein interactions in a wide variety of prokaryotic and eukaryotic cells, and is readily adapted to the instant methods. Guidance for using the alpha complementation system of LacZ in the subject methods is found in Eglen et al. (Comb. Chem. High Throughput Screen. 2003 6:381-7), Galarneau et al. (Nat. Biotechnol. 2002 20:619-22), Wehrman et al. (Proc. Natl. Acad. Sci. 2002 99:3469-74) and Blakely et al. (Nat. Biotechnol. 2000 18:218-22).

In other embodiments, the signal-producing system used may be a transcriptional activation system, where the two components of the system, if bound can direct expression of a reporter (e.g., a selectable marker, a counterselectable marker, a light-emitting protein, a colorigenic enzyme, or any other chemical, physical or biological signal-producing reporter), usually found in the nuclear genome of the cell. In other words, the subject intracellularized polypeptide may be linked to a first component of such a system, the subject binding partner may be linked to the second component of such a system, and the first and second components of the system, when bound in a complex form a transcription activator that can activate a reporter. Such systems include well-known "two-hybrid" and "reverse-two-hybrid" methodologies (e.g., Fields et al., Nature 1989 340:245-6; U.S. Pat. No. 5,667,973; Mendelsohn et al., Curr. Opin. Biotechnol. 1994 5:482-6; Vidal et al., Proc. Natl. Acad. Sci. 1996 93: 10315-10320; Vidal et al., Proc. Natl. Acad. Sci. 1996 93:10321-10326). Such methods rely on the in vivo activation of a reporter in a cell to detect interactions between proteins and/or polypeptides. By using "prey" and "bait" fusion proteins, the two-hybrid system allows researchers to detect interactions, and inhibitors thereof, between two proteins of interest (Chien et al., Proc. Natl. Acad. Sci. 1991 88:9578-82; Yang et al., Nucleic Acids Res. 1995 23:1152-6; Vidal et al., Proc. Natl. Acad. Sci. 1996 93:10321-10326). Such systems may utilize a modified GAL4 transcription systems, however, several similar systems are available for use in bacterial, yeast and mammalian cells.

In certain other embodiments, a counterselectable marker system may be used in which two polypeptides, if bound in a complex in a cell, will be toxic to the cell. Several such systems are known, and the ccd poison/antidote system of *E. coli* (Bahassi et al., J Biol. Chem. 1999 274:10936-44) is an example of a counterselectable marker system that may be readily employed in the subject methods. This system is based on two proteins encoded by *E. coli*'s F plasmid, CcdB, a toxin that inhibits DNA gyrase, and CcdA, an "antidote protein" that interacts with CcdB and neutralizes its toxicity. In the subject methods, a subject polypeptide could contain one of these ccd proteins, and a subject binding partner could contain the other ccd protein. Binding between a subject polypeptide and a subject binding partner in a cell can therefore be monitored by assaying cell survival.

Test Molecules

As mentioned briefly above, many embodiments of the invention involve test agents, e.g., nucleic acids encoding test polypeptides or small molecules. In an embodiment of particular interest, the test polypeptide is a conformationally restrained polypeptide. In many embodiments, conformationally restrained polypeptides are linear polypeptides containing a "presentation structure" that restricts the conformation of a sequence of amino acids, and thus presents the sequence in a conformationally restricted form. In general, such conformationally restricted polypeptides, nucleic acids encoding the same, and libraries thereof, are well known in the art (see, e.g., U.S. Pat. Nos. 6,562,617 and 6,455,247).

In certain embodiments, the conformationally restricted polypeptides are cyclic polypeptides, typically made in vivo by recombinant means, using known methodologies (see, e.g., Published US Patent 20040014100 for a detailed account of some of these methods).

In general, cyclic peptides are made in vivo using an intein-mediated system in which a nucleic acid encoding a recombinant intein fusion protein, i.e., a nucleic acid encoding, in order: a C-terminal intein domain, a nucleic acid encoding a test polypeptide, and a nucleic acid encoding an N-terminal intein domain, is introduced into a cell to produce a recombinant intein fusion protein. This recombinant intein protein autocatalyzes the excision and simultaneous cyclization of the test polypeptide lying between the C- and N-terminal intein domains. In vivo methods for cyclizing test polypeptide using intein-mediated systems are generally well understood in the art (Scott et al., Proc. Natl. Acad. Sci. 1999 96:13638-43 and reviewed by Xu et al., Methods 2001 24:257-77). Accordingly, when a nucleic acid encoding a cyclic polypeptide is referenced herein; a nucleic acid encoding a subject recombinant intein fusion protein, including C- and N-terminal intein domains and a test polypeptide therebetween, is described. When a cyclic polypeptide is referenced, the cyclic catalytic product of a subject recombinant intein fusion protein is described.

Typically, the subject test polypeptides, once produced, are present in the cytoplasm of the cell and not secreted. Accordingly, the subject test polypeptides are intracellular test polypeptides.

In particular embodiments, a subject test polypeptide may have a randomized amino acid sequence, and, in certain embodiments, may be part of a library of test polypeptides having randomized amino acid sequences. Such a library may be encoded by a corresponding library of polynucleotides, which library, when present in cells, may be a library of cells. In many embodiments, a subject library represents a structurally diverse population of randomized test polypeptides in a number sufficient to provide one or more cells containing a test polypeptide of interest (i.e., a test polypeptide having a desirable biological activity). Accordingly, such library is usually large enough so that at least one of its members will have affinity to a subject intracellularized polypeptide or binding partner thereof. In most embodiments, a subject library contains at least $10^4$, at least about $10^5$, at least about $10^6$, at least about $10^7$, at least $10^8$ or usually at least about $10^9$, usually up to about $10^{11}$ or $10^{12}$ or more different members.

In certain embodiments, a library of polynucleotides encoding all or a fraction of all possible 3 to 30-mer test polypeptides may be used in the subject methods. Libraries of smaller cyclic peptides, i.e., ranging from 3 to 10 amino acid in length, may also be used. Accordingly, in most embodiments an subject library may be contain test polypeptides of the following lengths: 3 amino acids, 4 amino acids, 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids, 25 amino acids, 26 amino acids, 27 amino acids, 28 amino acids, 29 amino acids and 30 amino acids, or any mixture thereof.

Methods for making conformationally restricted randomized polypeptides that may be linear or cyclic, nucleic acids encoding the same, and libraries thereof are known in the art (see, e.g., Published U.S. Patent Application 20040014100; Kinsella et al., J. Biol. Chem. 2002 277:37512-8 and U.S. Pat. Nos. 6,562,617 and 6,455,247, and many others) and need not be described here in any more detail than that set forth above.

Nucleic Acids

Since the genetic code and recombinant techniques for manipulating nucleic acids are known, and the amino acid sequences of the polypeptides described as above can be readily discerned, the design and production of nucleic acids encoding the polypeptide used in the subject methods are well within the skill of an artisan. In certain embodiments, standard recombinant DNA technology (Ausubel, et al, Short Protocols in Molecular Biology, 5th ed., Wiley & Sons, 2002; Sambrook, et al., Molecular Cloning: A Laboratory Manual, Third Edition, (2001) Cold Spring Harbor, N.Y.) methods are used. For example, cell surface receptor coding sequences may be isolated from a library of coding sequences (e.g., a cDNA library) using any one or a combination of a variety of recombinant methods that do not need to be described herein.

Subsequent substitution, deletion, and/or addition of nucleotides in the nucleic acid sequence encoding a protein may also be done use standard recombinant DNA techniques.

For example, site directed mutagenesis and subcloning may be used to introduce/delete/substitute nucleic acid residues in a polynucleotide encoding a polypeptide of interest. In other embodiments, PCR may be used. Nucleic acids encoding a polypeptide of interest may also be made by chemical synthesis entirely from oligonucleotides (e.g., Cello et al., Science (2002) 297:1016-8).

In certain embodiments, the codons of the nucleic acids encoding polypeptides of interest are optimized for expression in cells of a particular species, particularly a bacterial, yeast, insect, or mammalian, e.g., human, species.

In certain embodiments, nucleic acids encoding the subject polypeptides (i.e., an intracellularized polypeptide, a binding partner for the same, and a test polypeptide) are each typically present in an expression cassette that provides for expression in a host cell. These expression cassettes are typically present in one, two or three separate vectors (usually containing different selectable markers) for delivery of the expression cassettes in a host cell. Regulatory sequences (e.g., promoters and terminators), and vectors suitable use in many cells (e.g., mammalian, yeast, bacterial, insect, etc) are very well known in the art (Ausubel, et al, Short Protocols in Molecular Biology, 5th ed., Wiley & Sons, 2002; Sambrook, et al., Molecular Cloning: A Laboratory Manual, Third Edition, (2001) Cold Spring Harbor, N.Y.) and, accordingly, need not be discussed in any great detail.

Accordingly, the invention provides a cell containing a combination of subject nucleic acids. In many embodiments of the invention, the subject nucleic acids will be expressed in a host after the sequences have been operably linked to an expression control sequence, including, e.g. a promoter. The subject nucleic acids are also typically placed in an expression vector that can replicate in a host cell either as an episome or as an integral part of the host chromosomal DNA.

Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference). Vectors, including single, dual and triple expression cassette vectors are well known in the art (Ausubel, et al, Short Protocols in Molecular Biology, 5th ed., Wiley & Sons, 2002; Sambrook, et al., Molecular Cloning: A Laboratory Manual, Third Edition, (2001) Cold Spring Harbor, N.Y.). Suitable vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used. Vector copy number may be high (over 200 copies/cell), medium (50-199 copies/cell) or low (10-50, 2-9 or 1 copy/cell), as desired.

A variety of expression vectors are available to those in the art for purposes of producing a polypeptide of interest in a cell. One suitable vector is pCMV, which used in certain embodiments. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351. Bacterial expression systems are extremely well known (see, e.g., Ausubel, et al, Short Protocols in Molecular Biology, 5th ed., Wiley & Sons, 2002; Sambrook, et al., Molecular Cloning: A Laboratory Manual, Third Edition, (2001) Cold Spring Harbor, N.Y.) and not be discussed in any more detail.

The subject nucleic acids usually comprise an single open reading frame encoding a subject polypeptide of interest, however, in certain embodiments, since the host cell for expression of the polypeptide of interest may be a eukaryotic cell, e.g., a mammalian cell, such as a human cell, the open reading frame may be interrupted by introns. Subject nucleic acid are typically part of a transcriptional unit which may contain, in addition to the subject nucleic acid 3' and 5' untranslated regions (UTRs) which may direct RNA stability, translational efficiency, etc. The subject nucleic acid may also be part of an expression cassette which contains, in addition to the subject nucleic acid a promoter, which directs the transcription and expression of a polypeptide of interest, and a transcriptional terminator.

Eukaryotic promoters can be any promoter that is functional in a eukaryotic host cell, including viral promoters and promoters derived from eukaryotic genes. Exemplary eukaryotic promoters include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like. Viral promoters may be of particular interest as they are generally particularly strong promoters. In certain embodiments, a promoter is used that is a promoter of the target pathogen. Promoters for use in the present invention are selected such that they are functional in the cell type (and/or animal) into which they are being introduced. In certain embodiments, the promoter is a CMV promoter.

In certain embodiments, a subject vector may also provide for expression of a selectable marker. Suitable vectors and selectable markers are well known in the art and discussed in Ausubel, et al, (Short Protocols in Molecular Biology, 5th ed., Wiley & Sons, 2002) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thimydine kinase gene, the dihydrofolate reductase gene, the xanthine-guanine phosphoribosyl transferase gene, CAD, the adenosine deaminase gene, the asparagine synthetase gene, the antibiotic resistance genes, e.g. tetr, ampr, Cmr or cat, $kan^r$ or $neo^r$ (aminoglycoside phosphotransferase genes), the hygromycin B phosphotransferase gene, and the like.

In certain embodiments, a subject nucleic acid, particularly nucleic acid encoding a test polypeptide, may be part of a retroviral vector. A particularly well suited retroviral transfection system is described in Mann et al., supra: Pear et al., PNAS USA 90(18):8392-6 (1993); Kitamura et al., PNAS USA 92:9146-9150 (1995); Kinsella et al., Human Gene Therapy 7:1405-1413; Hofmann et al., PNAS USA 93:5185-5190; Choate et al., Human Gene Therapy 7:2247 (1996); and WO 94/19478; and references cited therein, all of which are incorporated by reference.

Promoters may be strong, weak, constitutive or inducible, as desired.

Host Cells

Suitable cells for use in the subject methods include prokaryotic, e.g., bacterial (for example *E. coli*) cells, as well as eukaryotic cells, e.g. an animal cell (for example an insect, mammal, fish, amphibian, bird or reptile cell), a plant cell (for example a maize or *Arabidopsis* cell), or a fungal cell (for example a *S. cerevisiae* cell). Suitable cells for the expression of polypeptides, and suitable vectors for use in those cells, are well known in the art and do not have to be described in any more detail (Ausubel, et al, *Short Protocols in Molecular Biology*, 5th ed., Wiley & Sons, 2002; Sambrook, et al., *Molecular Cloning: A Laboratory Manual*, Third Edition, (2001) Cold Spring Harbor, N.Y.)

In certain embodiments an animal host cell line is used, examples of which are as follows: monkey kidney cells (COS cells), monkey kidney CVI cells transformed by SV40 (COS-7, ATCC CRL 165 1); human embryonic kidney cells (HEK-293, Graham et al. J. Gen Virol. 36:59 (1977)); HEK-293T cells; baby hamster kidney cells (BHK, ATCC CCL 10); chinese hamster ovary-cells (CHO, Urlaub and Chasin, Proc. Natl. Acad. Sci. (USA) 77:4216, (1980); mouse sertoli cells (TM4, Mather, Biol. Reprod. 23:243-251 (1980)); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci. 383:44-68 (1982)); NIH/3T3 cells (ATCC CRL-1658); insect Sf9 cells, and mouse L cells (ATCC CCL-1). Relevant materials and methods will be followed according to the disclosure of U.S. Pat. No. 5,462,856 and U.S. Pat. No. 6,051,386.

Methods of Screening for Modulatory Agents

The invention provides methods of screening for agents, e.g., polypeptides that modulate binding between a subject polypeptide modified for intracellular presentation and, where present, a binding partner for that polypeptide. In an embodiment of particular interest, the subject methods involve assaying a population of cells, each of cell of the population containing: a) a recombinant nucleic acid encoding a polypeptide modified for intracellular presentation; b) a recombinant nucleic acid encoding a binding partner for said first polypeptide; and, c) a recombinant nucleic acid encoding a test polypeptide. In most embodiments, the assay is for identification of a conformationally restricted polypeptide present in a cell (i.e., an intracellular test polypeptide) that modulates binding between the intracellularized polypeptide and its binding partner.

While the binding of the intracellularized polypeptide and its binding partner may be assessed using traditional biochemical or physical means, (e.g., by immunoprecipitation, by cross-linking followed by immunodetection or co-purification, and the like) in certain embodiments, binding is typically assessed using a signal-producing system, as described above. Accordingly, in certain embodiments, the assay involves assaying a signal formed by a signal producing system.

Accordingly, in many embodiments, the subject screening methods typically involves assaying a plurality of cells containing a library of test polypeptides, and recombinant nucleic acid encoding an intracellularized polypeptide and its binding partner, for a signal that indicates a test polypeptide that modulates (i.e., increases or decreases) the level of molecular interaction between the intracellularized polypeptide and its binding partner. In an embodiment of particular interest, the test polypeptide is a conformationally restricted polypeptide.

Depending on the signal-producing system used, modulators of binding between the intracellularized polypeptide and its binding partner may be identified by observing an increase or decrease in a color or light signal, or, for example, an increase or decrease in cell survival, relative to control cells in the absence of a test polypeptide. In certain embodiments the assay may involve FACS sorting of cells with a desirable signal.

In many embodiments, the subject methods involve introducing expression cassettes for the above-recited polypeptides into the same host cell. As would be recognized by one of skill in the art, this could be done using a the vectors, a dual and a single expression cassette vector, or a triple expression cassette vector. Typically, if more than one expression vector is introduced into a cell, the expression vectors will have different selectable markers. Vectors having mono-, bi- or tri-cistronic expression cassettes may be employed.

Methods of introducing vectors into cells are well known in the art. Suitable methods include electroporation, particle gun technology, calcium phosphate precipitation, direct microinjection, and the like. The choice of method is generally dependent on the vector being used, the type of cell being transformed and the circumstances under which the transformation is taking place. A general discussion of these methods can be found in Ausubel, et al, Short Protocols in Molecular Biology, 5th ed., Wiley & Sons, 2002. In some embodiments lipofectamine and calcium mediated gene transfer technologies are used. Methods for introducing circular nucleic acids are also well known in the art and discussed in Ausubel, above. As is known in the art, this may be achieved by, for example, using a viral vector, e.g., a retroviral vector, and transfecting cell a sufficiently high titer of viral particles to introduce two different vectors into the cell.

After introduction of the expression cassettes into a cell, the cell is typically maintaining the cell under suitable conditions for polypeptide expression. To accomplish this, the cell may be incubated in suitable media (e.g., media containing antibiotics for selection of each of the transfected vectors) for a suitable period of time, e.g., 12-24 hr, 24-48 hr, or 48-96 hr or more. Transient or stable expression of the polypeptide may be carried out in this manner.

In particular embodiments, particularly those in which an intracellularized polypeptide and a binding partner that form a signal producing system are employed, cells containing the polypeptide and binding partner may be first screened to identify a cell suitable for the subject methods. For example, nucleic acids encoding an intracellularized polypeptide and a binding partner for that polypeptide may be introduced into cells using various promoters and/or vectors having differing copy numbers, and the cells screened for a cell producing a suitable signal. In most embodiments, the cell may have the highest signal. Once identified, that cell may be isolated, cultured, and used for future experiments (e.g., used for the testing of candidate agents). In one exemplary embodiment, a nucleic acid encoding an intracellularized polypeptide and a binding partner that form a FRET signal producing system are introduced into a cell, and the cells are screened to identify a cell with the highest FRET signal. This cell is isolated, cultured, and a library of agents may be introduced into the cultured cells.

After a suitable time period, binding between the intracellularized polypeptide and its binding partner is assayed, as discussed above.

In general, if a test polypeptide is an inhibitor of binding of an intracellularized polypeptide and its binding partner, a signal, as determined by a reporter activity for example, is usually reduced by greater than about 10%, greater than about 20%, greater than about 30%, greater than about 40%, greater than about 50%, greater than about 60%, greater than about 80%, greater than about 90%, greater than about 95%, greater than about 98%, or greater than about 99%, as compared to suitable controls, e.g., an identical cell lacking the test polypeptide.

If an agent is an increases binding between the intracellularized polypeptide and its binding partner, a signal, as determined by a reporter activity for example, is usually increased by greater than about 10%, greater than about 25%, greater than about 50%, greater than about 80%, greater than about 100%, greater than about 150%, greater than about 200%, greater than about 300%, greater than about 400%, greater than about 500%, or greater than about 1,000%, as compared to suitable controls, e.g., an identical cell lacking the test polypeptide.

In certain embodiments, a subject cell may be subjected to conditions, e.g., contacted with an agent such as a signaling molecule or a pathogen, to effect binding between the intracellularized receptor and its binding partner prior to assaying.

Polypeptides that modulate binding between an intracellularized receptor and its binding partner may specifically bind to an intracellularized receptor, to its binding partner, or any other molecule that is involved in or that may effect binding between the intracellularized receptor and its binding partner.

In other embodiments, a test polypeptide that interacts with an intracellularized polypeptide may be identified using similar methods as those described above, e.g., by using an intracellularized polypeptide and test polypeptide that, when bound together, produce a detectable signal. In other words, the members of a library of test polypeptides, e.g., conformationally restricted polypeptides, could individually be tested for binding to an intracellularized polypeptide by screening a library of cells containing a nucleic acid encoding an intracellularized polypeptide and a library of nucleic acids encoding test polypeptides using the methods described above.

In alternative embodiments, particularly those in which a signal producing system that produces a cytotoxic signal is employed, the expression cassettes for the intracellularized polypeptide and the binding partner thereof may be separately transfected into different populations of cells that can be mated (including equivalents thereof such as fused) to provide daughter cells containing both nucleic acids. In such embodiments, the vectors used typically contain different selectable markers, and both of those markers are selected for during mating. In these embodiments, one of the populations of cells will typically contain a library of test polypeptides. The populations are mated together, and daughter cells are assayed. In particular embodiments where a cytotoxic signal producing system is used, mating or fusion of the cells will typically result in death of the daughter cell, unless a test polypeptide that inhibits interaction between the components of the cytotoxic system is present in the cell. Accordingly, in certain embodiments, cells containing test polypeptides of interest will live to form colonies, whereas other cells will die.

Once a cell containing a test polypeptide of interest is identified, the polypeptide of interest may be characterized by sequencing its encoding nucleic acid, and made in greater quantities for further testing.

Test agents include or grammatical equivalents thereof, e.g., candidate agents, any molecule, e.g. proteins (which herein includes proteins, polypeptides, and peptides), small (i.e., 5-1000 Da, 100-750 Da, 200-500 Da, or less than 500 Da in size), organic or inorganic molecules, polysaccharides, polynucleotides, etc. Candidate agents encompass numerous chemical classes. In one embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, usually at least two of the functional chemical groups. The candidate agents often comprise cyclical carbon or heterocyclic structures and or aromatic or polyaromatic structures substituted with one or more chemical functional groups.

Candidate modulators are obtained from a wide variety of sources, as will be appreciated by those in the art, including libraries of synthetic or natural compounds. As will be appreciated by those in the art, the present invention provides a rapid and easy method for screening any library of candidate modulators, including the wide variety of known combinatorial chemistry-type libraries.

In one embodiment, candidate modulators are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods. As described in WO 94/24314, one of the advantages of the present method is that it is not necessary to characterize the candidate agent prior to the assay; only candidate modulators that affect binding need be identified.

Methods of Screening for Modulatory Conformationally Restricted Polypeptides Using a Plurality of Pools of Recombinant Cells Certain embodiments of the invention relate to a method for identifying a cell producing a biologically active conformationally restricted polypeptide. In general, this method involves: a) assaying a plurality of pools of different cells, the cells of each pool producing a plurality of different conformationally restricted test polypeptides, b) identifying a pool of cells producing a biologically active conformationally restricted test polypeptide, c) separating the cells in the identified pool, and d) assaying the isolated cells to identify a single cell producing a biologically active conformationally restricted test polypeptide. In many embodiments, the test polypeptides that are present intracellularly, and, accordingly, the method involves lysing samples of cells from the pools of cells to make cell lysates, and assaying the lysates for biological activity. This method is described in greater detail below.

In general, these embodiments involve separating a library of cells producing conformationally restricted test polypeptides, as described above, into a plurality of pools that each contains a different mixture of cells. The cells in each pool, collectively, produce a subset of the conformationally restricted test polypeptides of the library. In other words, the method generally involves a plurality (e.g., at least about 12, at least about 24, at least about 96, at least about 384, at least about 1000, at least about 2000, at least about 5000, or at least about 10,000 or more, usually up to 100,000 or more) of "aliquots" of a subject library, wherein each aliquot may contain more than about 2, more than about 4, more than about 12, more than about 24, more than about 100, more than about 200, more than about 500, more than about 1000, more than about 2000, more than about 5000, or more than about 10,000 or more, usually up to about 50,000 or more, of different members of the library.

In most embodiments, the subject pools of cells are present in a suitable microtiter plates, usually 24, 48 or 96-well microtiter plates. Typically, the cells present in those plates were cultured in those plates.

In most embodiments of this method, each pool of cells is typically assayed to identify cells producing test polypeptides that can modulate the activity of a cell surface receptor present on the surface a different cell, termed an "assay cell", herein. Typically, assay cells are mammalian cells, particularly human cells, and are usually cells grown in culture.

Assays for assessing the activity of cell surface receptor are generally extremely well known in the art, and can involve any one of a number of reporter systems, including reporters of gene expression reporters, and other colorimetric and light-producing reporters. Any biochemical or cell survival assay may also be used.

In certain embodiments, each pool of cells is assayed by taking a sample of the pool, lysing the cells in the pool to make a cells lysate, and assaying the cell lysate for cell surface receptor modulatory activity. In these embodiments, the cells in the sample are lysed using well known methods, e.g., mild detergent, enzymes, osmotic pressure, sonication, etc., to make lysates, and the lysates (which may be cleared by centrifugation, filtration or similar methods), contacted with an assay cell.

Assay cells may be assayed using any of the large number of known methods, including $^{35}S$ GTPγS binding assay, ATP hydrolysis assays, adenylyl cyclase assays (e.g., using the FLASH PLATE™ Adenylyl Cyclase kit from New England Nuclear; Cat. No. SMP004A), cAMP assays, reporter-based assays, AP1 reporter assays, SRF-LUC reporter assays, intracellular $IP_3$ accumulation assay, fluorometric imaging plate reader (FLIPR) assays for the measurement of intracellular calcium concentration, and melanophore assay (see, e.g., PCT patent publication no. WO 02/068600) and many others. In particular embodiments, assay cells are assayed for cell surface receptor activity.

If a pool of cells that produces a biologically active test polypeptide (i.e., a polypeptide having a cell surface receptor activity-modulatory activity) is identified, the identified pool of cells is typically re-assayed to identify a single cell (or cultured plurality thereof) that gave rise to the biological activity. In typically embodiments, the cells of the pool of cells are separated, usually cultured, and re-assayed for the same biological activity. Accordingly, in many embodiments, once a pool of interest is identified, the separated cells of that pool are isolated from each other, usually as single cells. In other embodiments, the cells are separated into pools of cells containing a lower (e.g., 10 or 100-fold lower) complexity than the starting pool of cells. These pools may be re-assayed and separated into single cells using the methods described above.

In most embodiments, therefore, the cells of a pool of cells identified as containing a cell producing a test polypeptide with biological activity are separated from each other to form a number of isolated single cells. While a number of dilution systems can achieve this separation, these separation steps are most easily done using any FACS or other cell sorter system. The single cells are typically cultured to provide a plurality of single cell cultures, and those cultures are assayed for biological activity using the same assay as previously used.

Once a single cell producing a biologically active test polypeptide is isolated using the above methods, the test polypeptide having biological activity may be characterized by sequencing its encoding nucleic acid, and made in greater quantities for further testing.

These methods find particular use for identifying biologically active cyclic polypeptides from libraries of randomized cyclic polypeptides.

UTILITY

The subject methods for identifying biologically active polypeptides find use in a variety of research and therapeutic protocols. For example, the polypeptides may be used in a method of modulating an activity of a cell, particularly a receptor-mediated activity of the cell, by contacting the cell with a polypeptide.

In other embodiments, polypeptides identified by the above methods may be used in to treat a subject for a surface receptor-related condition. In general, these methods involve administering to a subject in need thereof a therapeutic amount of a polypeptide identified by any of the above-described methods, wherein the polypeptide modulates a receptor and thereby treats a condition related to the receptor.

A variety of individuals are treatable according to the subject methods. Generally such individuals are mammals or mammalian, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the individuals will be humans.

Subject treatment methods are typically performed on individuals with such disorders or on individuals with a desire to avoid contracting such disorders.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the subject invention.

Example 1

Disrupting RANK:RANKL (TRANCE, OPGL, ODF) Interactions Using Cyclic Peptides

Polynucleotides encoding the RANK extracellular domain (amino acids 31-211) fused to YFP and the RANKL extracellular domain (amino acids 137-316) fused to GFP are cloned into a low copy number bicistronic bacterial expression vector with an ampicillin selectable marker. This generates a FRET pair designed to quench the 475 nm emission from CFP after stimulation at 425-450 nm in exchange for 550 nm light from YFP upon a successful interaction between RANK and RANKL. Both the RANK extracellular polypeptide (31-211) fused to human immunoglobulin Fc and the RANKL extracellular polypeptide (127-316) fused to glutathione-S-transferase have been successfully expressed in E.

*coli* as functional and soluble proteins (Hsu, H. et al. PNAS 96:3540-3545 1999; Ito, S. et al. JBC 277:6631-6636 2002). Bacteria are transformed with this vector, transformed bacteria are selected on agar plates, and also selected by FACs to identify and isolate clones that emit the highest emission ratio of 550 nm/475 nm upon stimulation with light at 425-450 nm. A clone optimized expression of both RANK and RANKL, and optimized FRET is selected and called the assay clone. This clone is made ultracompetent using standard protocols then transduced with a high-copy number bacterial expression vector expressing a cyclic peptide library (4, 5, 6, 7, 8+ mers) also containing a tetracycline resistance gene. Transformants are selected with both ampicillin and tetracycline to amplify the survival of the double transformants. A library of $10^{11}$-$10^{12}$ independent clones is generated. If a particular bacteria expresses a cyclic peptide that disrupts the RANKL-RANK interaction, it should also reduce the amount of FRET. The double transformants are screened by high-capacity FACS sorting (>50,000/sec) for loss of FRET and the clones with the appropriate phenotypes expanded in liquid culture or on agar. The expanded, selected clones can be rescreened multiple times by recloning the cyclic peptide sublibrary on tetracycline plates and retransforming the assay clone for FACS analysis. Once rescreening has been completed then individual cyclic clones could be tested and their efficiency quantitated.

The cyclic peptide DNA clones could then be used to scale up purified cyclic peptides from bacteria and tested in other assays to confirm that RANK-RANKL interactions can be disrupted and that these peptides inhibit RANK/RANKL activities such as osteoclast differentiation either in vitro or in vivo.

It is evident from the above discussion that the subject invention provides an important new means for identifying polypeptide modulators of cell surface polypeptides. As such, the subject methods and systems find use in a variety of different applications, including research, medical, therapeutic and other applications. Accordingly, the present invention represents a significant contribution to the art.

What is claimed is:

1. A cell comprising:
   a recombinant nucleic acid encoding a first polypeptide modified for intracellular presentation;
   and at least one of:
   a recombinant nucleic acid encoding a binding partner for said first polypeptide; and
   a recombinant nucleic acid encoding a test polypeptide.

2. The cell of claim 1, wherein said binding partner is a second polypeptide modified for intracellular presentation.

3. The cell of claim 2, wherein said first and second polypeptides modified for intracellular presentation are receptor subunits modified for intracellular presentation.

4. The cell of claim 1, wherein said cell comprises:
   a recombinant nucleic acid encoding a binding partner for said first polypeptide; and
   a recombinant nucleic acid encoding a test polypeptide.

5. The cell of claim 1, wherein the test polypeptide is a conformationally restricted polypeptide.

6. The cell of claim 5, wherein said conformationally restricted test polypeptide is a cyclic polypeptide.

7. The cell of claim 5, wherein said conformationally restricted test polypeptide is a fusion protein.

8. The cell of claim 5, wherein said conformationally restricted test polypeptide comprises a randomized amino acid sequence.

9. The cell of claim 1, wherein said first polypeptide and said binding partner, when bound in a polypeptide/binding partner complex, produce a signal.

10. The cell of claim 9, wherein said signal is a fluorescence resonance energy transfer signal.

11. The cell of claim 9, wherein said signal is a colorimetric signal.

12. The cell of claim 9, wherein said signal is a phenotypic signal.

13. The cell of claim 1, wherein said first polypeptide is a receptor, and said binding partner of said polypeptide is a ligand for said receptor.

14. The cell of claim 1, wherein said first polypeptide modified for intracellular presentation is associated with an intracellular cell membrane.

15. The cell of claim 1, wherein said first polypeptide modified for intracellular presentation comprises a transmembrane domain.

16. The cell of claim 1, wherein said first polypeptide modified for intracellular presentation is cytoplasmically soluble.

17. A library of cells, each cell having:
    a recombinant nucleic acid encoding a first polypeptide modified for intracellular presentation; and
    a recombinant nucleic acid encoding a test polypeptide.

18. The library of cells of claim 17, wherein each cell further comprises a nucleic acid encoding a binding partner for said first polypeptide.

19. The library of claim 17, wherein said test polypeptide is a conformationally restricted polypeptide.

20. The library of cells of claim 17, wherein the test polypeptides comprise randomized amino acid sequences.

21. A method of screening, comprising:
    assaying a population of cells each cell of said population comprising:
    a recombinant nucleic acid encoding a first polypeptide modified for intracellular presentation;
    a recombinant nucleic acid encoding a binding partner for said first polypeptide; and,
    a recombinant nucleic acid encoding a test polypeptide;
    said assaying being for identification of a test polypeptide that modulates binding between said first polypeptide and said binding partner.

22. The method of claim 21, wherein the test polypeptide is a conformationally restrained polypeptide.

23. The method of claim 21, wherein said polypeptide modified for intracellular presentation and said binding partner, when complexed, produce a signal, and wherein said assaying comprises assaying said signal.

24. The method of claim 23, wherein said signal is an optical signal.

25. The method of claim 21, wherein said assaying involves FACS sorting of said cells.

26. The method of claim 21, wherein said first polypeptide is a subunit of a receptor, and each cell further comprises a recombinant nucleic acid encoding a ligand for said receptor.

27. A method for identifying a cell producing a biologically active polypeptide, comprising: lysing samples of cells from pools of cells to make cell lysates; assaying a plurality of pools of different lysed cells, the lysed cells of each pool producing a plurality of different conformationally restricted test polypeptides, thereby identifying a pool of cells producing a biologically active conformationally restrained test polypeptide; separating the cells in said identified pool; and assaying said isolated cells to identify a cell producing said biologically active conformationally restricted test polypeptide.

28. The cell of claim 27, wherein said conformationally restricted test polypeptide is a cyclic polypeptide.

29. The cell of claim 27, wherein said conformationally restricted test polypeptide is a fusion protein.

30. The method of claim 27, wherein said isolated cells are cultured prior to assaying said isolated cells.

31. The method of claim 27, wherein said biological activity is modulation of a surface-bound receptor on the surface of a mammalian cell.

32. The method of claim 27, wherein the conformationally restricted test polypeptides comprise a randomized sequence.

33. A method of modulating an activity to a cell, comprising: contacting said cell with a polypeptide identified by the method of claim 21.

34. The method of claim 33, wherein said activity is a receptor-mediated activity.

35. A method of treating a subject for a receptor-related condition comprising: administering to said subject a polypeptide identified by the method of claim 21, wherein said polypeptide modulates said receptor and thereby treats said receptor-related condition.

* * * * *

UNITED STATES PATENT AND TRADEMARK OFFICE
CERTIFICATE OF CORRECTION

| | | |
|---|---|---|
| PATENT NO. | : 7,745,196 B1 | Page 1 of 1 |
| APPLICATION NO. | : 11/067065 | |
| DATED | : June 29, 2010 | |
| INVENTOR(S) | : Brian Wong | |

It is certified that error appears in the above-identified patent and that said Letters Patent is hereby corrected as shown below:

In the Claims

In column 28, line 1, the word "to" should be replaced with -- of --.

Signed and Sealed this

Thirtieth Day of November, 2010

David J. Kappos
*Director of the United States Patent and Trademark Office*